(12) United States Patent
Balmforth et al.

(10) Patent No.: US 11,920,192 B2
(45) Date of Patent: Mar. 5, 2024

(54) SINGLE NUCLEOTIDE DETECTION METHOD AND ASSOCIATED PROBES

(71) Applicant: LIGHTCAST DISCOVERY LTD, Cambridge (GB)

(72) Inventors: Barnaby Balmforth, Cambridge (GB); Cameron Alexander Frayling, Cambridge (GB); Mark Dethlefsen, Cambridge (GB)

(73) Assignee: LIGHTCAST DISCOVERY LTD, Cambridge (GB)

( * ) Notice: Subject to any disclaimer, the term of this patent is extended or adjusted under 35 U.S.C. 154(b) by 375 days.

(21) Appl. No.: 16/613,593

(22) PCT Filed: May 15, 2018

(86) PCT No.: PCT/EP2018/062545
§ 371 (c)(1),
(2) Date: Nov. 14, 2019

(87) PCT Pub. No.: WO2018/210823
PCT Pub. Date: Nov. 22, 2018

(65) Prior Publication Data
US 2020/0208210 A1 Jul. 2, 2020

(30) Foreign Application Priority Data

May 15, 2017 (EP) .................................... 17171168
Oct. 23, 2017 (GB) .................................... 1717417

(51) Int. Cl.
*C12Q 1/6869* (2018.01)
*C12Q 1/6823* (2018.01)

(52) U.S. Cl.
CPC .......... *C12Q 1/6869* (2013.01); *C12Q 1/6823* (2013.01); *C12Q 2521/101* (2013.01); *C12Q 2521/301* (2013.01); *C12Q 2521/319* (2013.01); *C12Q 2525/125* (2013.01); *C12Q 2525/307* (2013.01); *C12Q 2537/149* (2013.01); *C12Q 2563/107* (2013.01); *C12Q 2563/159* (2013.01)

(58) Field of Classification Search
CPC ........ C12Q 2521/319; C12Q 2521/301; C12Q 2537/149; C12Q 2521/101; C12Q 1/6823; C12Q 1/6869; C12Q 2525/307; C12Q 2563/107; C12Q 2563/159; C12Q 2521/307; C12Q 2525/125
See application file for complete search history.

(56) References Cited

U.S. PATENT DOCUMENTS

| | | |
|---|---|---|
| 5,674,743 A | 10/1997 | Ulmer |
| 6,268,146 B1 | 7/2001 | Shultz et al. |
| 6,361,942 B1 | 3/2002 | Coull et al. |
| 9,771,615 B2 | 9/2017 | Frayling et al. |
| 9,856,528 B2 | 1/2018 | Balmforth et al. |
| 10,000,802 B2 | 6/2018 | Frayling et al. |
| 2003/0138831 A1 | 7/2003 | Kwagh et al. |
| 2003/0187237 A1 | 10/2003 | Chan et al. |
| 2007/0015176 A1 | 1/2007 | Lao et al. |
| 2007/0243634 A1 | 10/2007 | Pamula et al. |
| 2007/0269817 A1 | 11/2007 | Shapero |
| 2008/0003142 A1 | 1/2008 | Link et al. |
| 2009/0246788 A1 | 10/2009 | Albert et al. |
| 2009/0280475 A1 | 11/2009 | Pollack et al. |
| 2010/0184020 A1 | 7/2010 | Beer |
| 2012/0164633 A1 | 6/2012 | Laffler |
| 2015/0232925 A1 | 8/2015 | Frayling et al. |
| 2015/0247192 A1 | 9/2015 | Frayling et al. |
| 2015/0275293 A1 | 10/2015 | Frayling et al. |

(Continued)

FOREIGN PATENT DOCUMENTS

| | | |
|---|---|---|
| EP | 0 878 554 | 11/1998 |
| WO | 94/18218 | 8/1994 |
| WO | 03/046216 | 6/2003 |

(Continued)

OTHER PUBLICATIONS

NEB Product Guideline [retrieved on-line, February 2, retrieved from: https://www.neb.com/tools-and-resources/usage-guidelines/heat-inactivation, pp. 1-12] (Year: 2022).*
International Search Report dated Jun. 20, 2018 in International (PCT) Application No. PCT/EP2018/062545.
Extended European Search Report dated Aug. 10, 2017 in European Application No. 17171168.2.
Nutiu et al., "Structure-Switching Signaling Aptarners: Transducing Molecular Recognition into Fluorescence Signaling", Chemistry—A European Journal, Vol. 10, 2004, pp. 1868-1876.

(Continued)

*Primary Examiner* — Young J Kim
(74) *Attorney, Agent, or Firm* — Wenderoth, Lind & Ponack, L.L.P.

(57) ABSTRACT

A method of sequencing a nucleic acid comprising (1) generating a stream of single nucleoside triphosphates by progressive enzymatic digestion of the nucleic acid; (2) producing at least one oligonucleotide used probe by reacting, in the presence of a polymerase, at least one of the single nucleoside triphosphates with a corresponding biological probe comprising (a) a first single-stranded oligonucleotide including an exonuclease blocking-site, a restriction endonuclease recognition-site located on the 5' side of the blocking-site and including a single nucleotide capture-site e, and at least one fluorophore region and (b) a second and optionally a third single-stranded oligonucleotide each separate from the first oligonucleotide; (3) cleaving the first oligonucleotide strand of the used probe at the recognition-site with a restriction endonuclease; (4) digesting the first oligonucleotide component with an enzyme to yield fluorophores in a detectable state and (5) detecting the fluorophores released in step (4).

Figure 1:
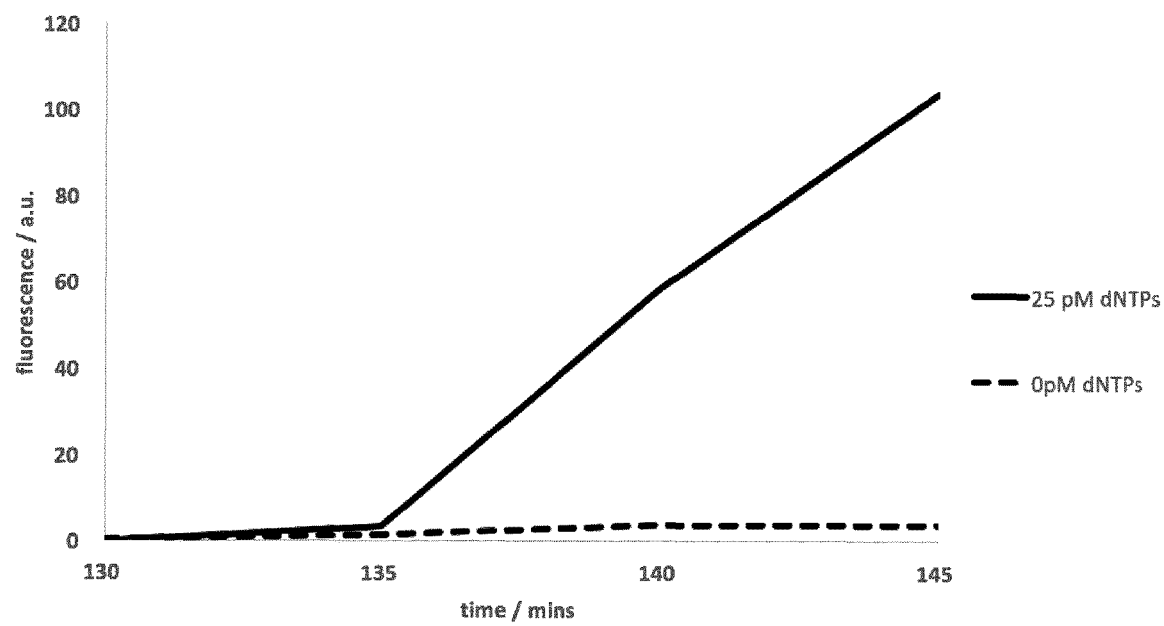

10 Claims, 1 Drawing Sheet
Specification includes a Sequence Listing.

(56) References Cited

U.S. PATENT DOCUMENTS

| | | |
|---|---|---|
| 2016/0040223 A1 | 2/2016 | Frayling et al. |
| 2016/0040224 A1 | 2/2016 | Frayling et al. |

FOREIGN PATENT DOCUMENTS

| | | | |
|---|---|---|---|
| WO | 03/080861 | 10/2003 | |
| WO | 2004/002627 | 1/2004 | |
| WO | 2006/088911 | 8/2006 | |
| WO | 2006/115570 | 11/2006 | |
| WO | 2009/085215 | 7/2009 | |
| WO | 2010/077859 | 7/2010 | |
| WO | 2013/037962 | 3/2013 | |
| WO | 2014/053853 | 4/2014 | |
| WO | 2014/053854 | 4/2014 | |
| WO | 2014/111723 | 7/2014 | |
| WO | 2014/167323 | 10/2014 | |
| WO | 2014/167324 | 10/2014 | |
| WO | WO-2014167323 A1 * | 10/2014 | ........ B01L 3/502784 |
| WO | 2015/121675 | 8/2015 | |
| WO | 2016/012789 | 1/2016 | |
| WO | 2017/005789 | 1/2017 | |

OTHER PUBLICATIONS

Stephan et al., "Towards a general procedure for sequencing single DNA molecules", Journal of Biotechnology, vol. 86, 2001, pp. 255-267.

Hagan Bayley, "Sequencing single molecules of DNA", Current Opinion in Chemical Biology, vol. 10, 2006, pp. 628-637.

Boles et al., "Droplet-Based Pyrosequencing Using Digital Microfluidics", Analytical Chemistry, vol. 83, 2011, pp. 8439-8447.

Theberge et al., "Microdroplets in Microfluidics: An Evolving Platform for Discoveries in Chemistry and Biology", Angeandte Chemie International, vol. 49, 2010, pp. 5846-5868.

Eicher et al., "Microfluidic devices for diagnostic applications", Expert Review of Molecular Diagnostics, vol. 11, No. 5, 2011, pp. 505-519.

Schweitzer et al., "Immunoassays with rolling circle DNA amplification: A versatile platform for ultrasensitive antigen detection", Proceedings of the National Academy of Sciences, USA, vol. 97, No. 18, 2000, p. 10113-10119.

Deutscher et al., "Enzymatic Synthesis of Deoxyribonuleic Acid", The Journal of Biological Chemistry, vol. 244, No. 11, 1969, pp. 3019-3028.

Liu et al., "Pyrophosphorolysis-Activated Polymerization (PAP): Application to Allele-Specific Amplification", BioTechniques, vol. 29, 2000, pp. 1072-1083.

Kunkel et al., "On the Fidelity of DNA Synthesis", The Journal of Biological Chemistry, vol. 261, No. 29, 1986, pp. 13610-13616.

Fan et al., "Highly parallel genomic assays", Nature Review Genetics, vol. 7, 2006, pp. 632-644.

Cui et al., "A dual amplification fluorescent strategy for sensitive detection of DNA methyltransferase activity based on strand displacement amplification and DNAzyme amplification", Biosensors and Bioelectronics, vol. 77, 2016, pp. 650-655.

Bao et al., "Total Biosynthesis of Deoxynucleoside Triphosphates Using Deoxynucleoside Monophosphate Kinases for PCR Application", Biotechnology and Bioengineering, vol. 98, No. 1, 2007, pp. 1-11.

* cited by examiner

SINGLE NUCLEOTIDE DETECTION METHOD AND ASSOCIATED PROBES

This invention relates to a method and associated biological probes for detecting and characterising single nucleotides. It is especially suitable for use in the sequencing of DNA or RNA.

Next generation sequencing of genetic material is already making a significant impact on the biological sciences in general and medicine in particular as the unit cost of sequencing falls in line with the coming to market of faster and faster sequencing machines.

In our previous applications WO 2014/053853, WO 2014/053854, WO2014/167323, WO2014/167324, WO2014/111723, WO2015/121675 and WO2017/005789, we have described a new sequencing method which involves progressive digestion of a polynucleotide analyte to generate an ordered stream of single nucleotides, preferably a stream of single nucleoside triphosphates, each of which can be captured one-by-one into corresponding droplets in a microdroplet stream. Thereafter, each droplet can be chemically and/or enzymatically manipulated to reveal the particular single nucleotide it originally contained. In one embodiment, these chemical and/or enzymatic manipulations comprise a method involving the use of one or more two-component oligonucleotide probe types each of which is adapted to be able to selectively capture one of the single nucleotide types from which the analyte is constituted. Typically, in each of such probe types, one of the two oligonucleotide components comprises characteristic fluorophores and in the probe's unused state the ability of these fluorophores to fluoresce remains extinguished by virtue of the presence of quenchers located close-by or by self-quenching. In use, when the probe has captured its corresponding single nucleotide, it is rendered susceptible to subsequent exonucleolysis thereby liberating the fluorophores from the quenchers and/or each other enabling them to fluoresce freely. By this means, the original single nucleotide present in each droplet can be inferred indirectly by spectroscopic means.

Variants of this method have been described in other of our pending applications including WO201405385 and WO2016012789; the latter involving the use of a three-component probe. In particular, WO2016012789 describes an improved method characterised by the steps of (1) generating a stream of single nucleoside triphosphates by progressive digestion of the nucleic acid; (2) producing at least one substantially double-stranded oligonucleotide used probe by reacting in the presence of a polymerase and a ligase at least one of the single nucleoside triphosphates with a corresponding probe comprising (a) a first single-stranded oligonucleotide labelled with e.g. characteristic fluorophores in an undetectable state and (b) second and third single-stranded oligonucleotides capable of hybridising to complementary regions on the first oligonucleotide; (3) digesting the used probe with an enzyme having double-stranded exonucleolytic activity to yield the fluorophores in a detectable state and a single-stranded fourth oligonucleotide which is at least in part the sequence complement of the first oligonucleotide; (4) reacting the fourth oligonucleotide with another first oligonucleotide to produce a substantially double-stranded oligonucleotide product corresponding to the used probe; (5) repeating steps (3) and (4) in a cycle and (6) detecting the fluorophores released in each iteration of step (3). This method has the advantage that by iterating steps (3) and (4) in a cycle the fluorescence signal can be made to grow strongly thereby improving the overall sensitivity and therefore reliability of nucleotide detection. In one embodiment, the second and third oligonucleotides are linked so that, after nucleotide capture, they form a closed-loop single-stranded oligonucleotide component which is advantageously resistant to exonucleolysis.

As regards other prior art, Fan et al in Nature Reviews Genetics 7 (8) 632-644 (2006) have provided a general review of the development of methods and platforms that have enabled highly parallel genomic assays for genotyping, copy-number measurements, sequencing, detecting loss of heterozygosity, allele-specific expression and methylation. FIG. 2a of this review schematically shows the use of a circularizable probe with 3' and 5' ends that anneal upstream and downstream of a site of single nucleotide polymorphism (SNP) on an analyte thereby leaving a gap which is subsequently filled with a nucleotide which is the complement of the SNP to form a complete circular probe which may then be amplified after release. However unlike our method, the nucleotide which is captured during the filling process is not obtained directly from the analyte itself.

WO03080861 discloses a process wherein a nucleic acid analyte is subjected to progressive pyrophosphorolysis in the presence of a nucleotide-specific reactive label which attaches directly to the nucleotide as it is released. Not only is this quite different from the method we employ, but in practice the fluorescence signal measured when the labelled nucleotides are subsequently interrogated would likely be too weak to enable reliable identification above the associated background noise.

Finally, WO9418218 teaches a DNA sequencing method in which the analyte is subjected to progressive exonucleolysis to generate a stream of single nucleotide diphosphates or monophosphates which are then incorporated into a fluorescence-enhancing matrix before being detected. Not only is this a completely different approach to the one we describe, but any signal generated would likely be too weak to be reliably detected and identified.

One disadvantage of the exonucleolysis-based methods described above is that the rate of generation of the fluorescence signal is limited by the speed of the digestion stage and that the specificity of the exonuclease limits the signal-to-noise level achievable. Whilst this is by no means fatal to the utility of the method, it nevertheless remains highly desirable from a technical perspective to reduce the incubation period associated with this growth in fluorescence and improve the signal-to-noise to enable faster, more accurate sequencing; especially where long sequencing reads are contemplated. This we have now achieved by a combination of exonucleolytic digestion of the used probe with selective endonucleolytic cleaving of the strand bearing the quenched fluorophores. Thus, according to a first aspect of the present invention, there is provided a method of sequencing a nucleic acid characterised by the steps of (1) generating a stream of single nucleoside triphosphates by progressive enzymatic digestion of the nucleic acid; (2) producing at least one oligonucleotide used probe by reacting, in the presence of a polymerase, at least one of the single nucleoside triphosphates with a corresponding biological probe comprising (a) a first single-stranded oligonucleotide including an exonuclease blocking-site, a restriction endonuclease recognition-site located on the 5' side of the blocking-site and including a single nucleotide capture-site for capturing the single nucleoside triphosphate, and at least one fluorophore region located on the 5' side of the recognition-site arranged so as to render the fluorophore(s) quenched and (b) a second and optionally a third single-stranded oligonucleotides each separate from the first oligonucleotide and capable of hybridising to complementary regions on the first oligonucleotide flanking the 3' and 5' sides of the capture-site; (3) cleaving the first oligonucleotide strand of the used probe at the recognition-site with a restriction endonuclease to create a first oligonucleotide component bearing the fluorophores; (4) digesting the first oligonucleotide component with an enzyme having 3'-5' exonucleolytic activity to yield fluorophores in a detectable state and (5) detecting the fluorophores released in step (4).

According to a second aspect of the invention, there is provided a method of sequencing a nucleic acid characterised by the steps of (1) generating a stream of single nucleoside triphosphates by progressive enzymatic digestion of the nucleic acid; (2) producing at least one oligonucleotide used probe by reacting, in the presence of a polymerase, at least one of the single nucleoside triphosphates with a corresponding biological probe comprising (a) a first single-stranded oligonucleotide including an exonuclease blocking-site, a restriction endonuclease recognition-site located on the 3' side of the blocking-site and including a single nucleotide capture-site for capturing the single nucleoside triphosphate, and at least one fluorophore region located on the 3' side of the recognition-site arranged so as to render the fluorophore(s) quenched and (b) a second and optionally a third single-stranded oligonucleotides each separate from the first oligonucleotide and capable of hybridising to complementary regions on the first oligonucleotide flanking the 3' and 5' sides of the capture-site; (3) cleaving the first oligonucleotide strand of the used probe at the recognition-site with a restriction endonuclease to create a first oligonucleotide component bearing the fluorophores; (4) digesting the first oligonucleotide component with an enzyme having 5'-3' exonucleolytic activity to yield fluorophores in a detectable state and (5) detecting the fluorophores released in step (4).

In one preferred embodiment, steps (2) and (3) are iterated as described below to increase significantly the number of fluorophores released for detection in step (5).

Step (1) of the method of the present invention comprises generating a stream of single nucleoside triphosphates from a nucleic acid analyte by progressive enzymatic digestion. In one embodiment, this can be achieved by progressive exonucleolysis of the analyte followed by the action of a kinase on the single nucleoside monophosphates obtained (see for example Biotechnology and Bioengineering by Bao and Ryu (DOI 10.1002/bit.21498). Preferably, however, the nucleoside triphosphates are produced directly from the analyte by progressive pyrophosphorolysis. The analyte employed in this step is suitably a double-stranded polynucleotide the length of which can in principle be unlimited; for example including up to the many millions of nucleotides found in a human gene or chromosome fragment. Typically, however, the polynucleotide will be at least 50, preferably at least 150 nucleotide pairs long; suitably it will be greater than 500, greater than 1000 and in many cases thousands of nucleotide pairs long. The analyte itself is preferably RNA or DNA of natural origin (e.g. derived from a plant, animal, bacterium or a virus) although the method can also be used to sequence synthetically-produced RNA or DNA or other nucleic acids made up wholly or in part of nucleotides whose nucleobases are not commonly encountered in nature; i.e. nucleobases other than adenine (A), guanine (G), cytosine (C), thymine (T) and uracil (U). Examples of such nucleobases include 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine and 2-O-methyluridine. In the case of DNA the single nucleoside triphosphates generated are deoxyribonucleoside triphosphates whilst in the case of RNA they are ribonucleoside triphosphates.

In one embodiment of the method, step (1) further comprises a first sub-step of attaching the analyte to a substrate. Typically, this substrate comprises a microfluidic surface, a micro-bead or a permeable membrane; for example one made of glass or a non-degradable polymer. Preferably, the substrate further comprises a surface specifically adapted to receive the analyte. There are many ways in which the analyte can be attached to such surfaces any of which can in principle be used in this sub-step. For example, one method involves priming a glass surface with a functionalised silane such as an epoxysilane, an aminohydrocarbylsilane or a mercaptosilane. The reactive sites so generated can then be treated with a derivative of the analyte which has been modified to include a terminal amine, succinyl or thiol group.

In another embodiment of step (1), the analyte is pyrophosphorolysed to generate a stream of single nucleoside triphosphates the order of which corresponds to that of the sequence of the analyte. Such pyrophosphorolysis may be carried out at a temperature in the range 20 to 90° C.; for example in the presence of a reaction medium comprising a suitable polymerase. Preferably it is carried out under conditions of continuous flow so that the single nucleoside triphosphates are continually removed from the reaction zone as they are liberated. Most preferably, the pyrophosphorolysis is carried out by causing an aqueous buffered medium containing the enzyme and the other typical additives to continuously flow over the surface to which the analyte is bound.

In yet another embodiment, the enzyme used is one which can cause progressive 3'-5' pyrophosphorolytic digestion of the analyte to yield a stream of nucleoside triphosphates with high fidelity and at a reasonable reaction rate. Preferably, this digestion rate is as fast as possible and in one embodiment is in the range 1 to 50 nucleoside triphosphates per second.

Further information about the pyrophosphorolysis reaction as applied to the digestion of polynucleotides can be found for example in J. Biol. Chem. 244 (1969) pp. 3019-3028 to which the reader is directed. Suitably, the pyrophosphorolytic digestion is carried out in the presence of a medium which further comprises for example pyrophosphate anion and magnesium cations; preferably in millimolar concentrations.

In step (2) of the method of the present invention, at least one single nucleoside triphosphate molecule, preferably each single nucleoside triphosphate in the stream, is reacted in the presence of a polymerase and optionally a ligase with a probe to generate a used probe duplex which in one embodiment where a ligase is additionally employed is a discrete substantially double-stranded oligonucleotide. Preferably, before this step is carried out the product of step (1) is treated with a pyrophosphatase, to hydrolyse any residual pyrophosphate anion.

The polymerase used in step (1) is suitably selected from the group consisting of those which show essentially neither exo- nor endonuclease activity under the reaction conditions. Examples of polymerases which can be advantageously used include, but are not limited to, the prokaryotic pol 1 enzymes or enzyme derivatives obtained from bacteria such as *Escherichia coli* (e.g. Klenow fragment polymerase), *Thermus aquaticus* (e.g. Taq Pol), *Bacillus stearothermophilus, Bacillus caldovelox* and *Bacillus caldotenax*. Any suitable ligase can in principle be used in this step if required.

The biological probe employed in step (2) is comprised of two or preferably three components; (a) a first single-stranded oligonucleotide labelled with characteristic fluorophores in an undetectable state and (b) a second and optionally a third unlabelled single-stranded oligonucleotides each separate from the first oligonucleotide and capable of hybridising to complementary regions on the first oligonucleotide. In one three-component embodiment, the second and third oligonucleotides are discrete entities whilst in another they are oligonucleotide regions linked by means of a linker-region. In this latter case, in one embodiment the linker-region links ends of the second and third oligonucleotide regions. The linker-region can in principle be any divalent group but is conveniently itself another oligonucleotide region. In one embodiment this oligonucleotide linker-region is unable to hybridise substantially to the first oligonucleotide.

The separate first, second and third oligonucleotides are chosen so that in step (2) the second and third oligonucleotides can hybridise respectively to 3' side and 5' side flanking regions on the first oligonucleotide which themselves are juxtaposed either side of a restriction endonuclease recognition-site which includes a capture-site comprising the single nucleotide whose nucleobase is complementary to that borne by the nucleoside triphosphate to be detected by the probe. This makes the probe highly selective for this particular nucleoside triphosphate. Thus, for example, if the analyte is derived from DNA and the first, second and third oligonucleotides are comprised of deoxyribonucleotides, the capture-site will be highly selective for deoxyadenosine triphosphate if the capture-site comprises a nucleotide bearing a thymine nucleobase. In one useful embodiment of the invention therefore, step (2) may be carried out in the presence of a probe system comprised of a plurality of probe types; for example one, two, three, four or more probe types each of which comprises a first oligonucleotide having a different capture-site characteristic of the set of various different nucleobases sought and different detectable elements attached thereto.

Typically, the first oligonucleotide is up to 150 nucleotides long, preferably between 10 and 100 nucleotides. In one embodiment the second oligonucleotide is shorter than the complementary 3' side flanking region of the first oligonucleotide by at least one nucleotide. In another, there is at least a single nucleotide mismatch between the 3' end of the first oligonucleotide and the nucleotide opposite it on the second oligonucleotide to prevent the nucleoside triphosphate being captured at this point. Similarly, in one embodiment the third oligonucleotide is longer than the complementary 5' side flanking region of the first oligonucleotide by at least one nucleotide, while in another there is at least a single nucleotide mismatch between the 3' end of the third oligonucleotide and the nucleotide opposite it in the first oligonucleotide to prevent the nucleoside triphosphate being captured at this point.

It is a feature of the first oligonucleotide that it is labelled with a fluorophore region comprised of its own unique and/or characteristic type of fluorophore(s) and that these fluorophore(s) are arranged so as to be substantially undetectable when the probe is in an unused state. Preferably they are arranged to be essentially non-fluorescing at those wavelengths where the fluorophores are designed to be detected. Thus, although a fluorophore may exhibit general, low-level background fluorescence across a wide part of the electromagnetic spectrum, there will typically be one or a small number of specific wavelengths or wavelength envelopes where the intensity of the fluorescence is at a maximum. It is at one or more of these maxima where the fluorophore is characteristically detected that essentially no fluorescence should occur. In the context of this patent, by the term 'essentially non-fluorescing' or equivalent wording is meant that the intensity of fluorescence of the total number of fluorophores attached to the first oligonucleotide at the relevant characteristic wavelength or wavelength envelope is less than 25%; preferably less than 10%; more preferably less than 1% and most preferably less than 0.1% of the corresponding intensity of fluorescence of an equivalent number of free fluorophores.

In principle, any method can be used to ensure that in the first oligonucleotide's unused state the fluorophores are essentially non-fluorescing. In one embodiment this is achieved by arranging the fluorophores in close proximity to each other so that they quench one another (self-quenching arrangement). In another embodiment, the fluorophore region(s) further include separate quenchers in close proximity to the fluorophores by means of which the same outcome can be achieved. In the context of this patent, what constitutes 'close proximity' between fluorophores or between fluorophores and quenchers will depend on the particular fluorophores and possibly the structural characteristics of the first oligonucleotide. Consequently, it is intended that this term should be construed with reference to the required outcome rather than any particular structural arrangement of the various elements within the two regions. However, and for the purposes of providing exemplification only, it is pointed out that when adjacent fluorophores are separated by a distance corresponding to the characteristic Forster distance (typically less than 5 nm) sufficient quenching will generally be achieved.

As regards the fluorophores themselves, they can in principle be chosen from any of those conventionally used in the art including but not limited to xanthene moieties e.g. fluorescein, rhodamine and their derivatives such as fluorescein isothiocyanate, rhodamine B and the like; coumarin moieties (e.g. hydroxy-, methyl- and aminocoumarin) and cyanine moieties such as Cy2, Cy3, Cy5 and Cy7. Specific examples include fluorophores derived from the following commonly used dyes: Alexa dyes, cyanine dyes, Atto Tec dyes, and rhodamine dyes. Examples also include: Atto 633 (ATTO-TEC GmbH), Texas Red™, Atto 740 (ATTO-TEC GmbH), Rose Bengal, Alexa Fluor™ 750 $C_5$-maleimide (Invitrogen), Alexa Fluor™ 532 $C_2$-maleimide (Invitrogen) and Rhodamine Red $C_2$-maleimide and Rhodamine Green as well as phosphoramadite dyes such as Quasar 570. Alternatively, a quantum dot or a near infra-red dye such as those supplied by LI-COR Biosciences can be employed and should be considered to be 'fluorophores' for the purposes of interpreting this patent. The fluorophore is typically attached to the first oligonucleotide via a nucleobase using chemical methods known in the art.

Suitable quenchers include those which work by a Förster resonance energy transfer (FRET) mechanism. Examples of commercially available quenchers which can be used in association with the above mentioned-fluorophores include but are not limited to DDQ-1, Dabcyl, Eclipse, Iowa Black FQ and RQ, IR Dye-QC1, BHQ-0, BHQ-1, -2 and -3 and QSY-7 and -21.

It is another feature of the first oligonucleotide that it includes an exonuclease blocking-site on either the 3' or 5' side of the recognition-site depending on which of the two methods described above is being employed. In one embodiment, the first oligonucleotide may include such blocking-sites adjacent either or both ends. In principle the blocking-site can be any region which by virtue of its chemical constitution renders the first oligonucleotide resistant to exonucleolysis at that point. Such regions may for example include phosphorothioate linkers, oligonucleotide spacers (e.g. Spacer 3, Spacer 9, Spacer 18, dSpacer and the like), 2'-O-methyl RNA bases, inverted bases, desthiobiotin-TEG, dithiol, hexanediol, and quenchers (e.g. BHQ).

In one embodiment, the exonuclease blocking-site can be achieved by rendering the first oligonucleotide circular; i.e. a closed-loop. In another embodiment, the second and/or third oligonucleotides will also be provided with similar exonuclease blocking-sites.

It is yet another feature of the first oligonucleotide that it includes a restriction endonuclease recognition-site which includes the capture-site referred to above. This recognition-site is arranged on either (1) the 5' side of the exonuclease blocking-site and the 3' side of fluorophore region or (2) the 3' side of the exonuclease blocking-site and the 5' side of the fluorophore region depending on which of the two methods described above is employed. In one embodiment, where more than one first oligonucleotide type is employed, it is preferred that each differently labelled first oligonucleotide nevertheless comprises the same recognition-site so that only one restriction endonuclease need be employed. For many applications therefore, it will be preferred that the recognition-site is comprised of a sequence containing at least one of each of the characteristic nucleotides of RNA or DNA as the case may be.

Step (2) is suitably carried out by contacting each single nucleoside triphosphate in the stream with the enzymes and one or more probes as described above at a temperature in the range 20 to 80° C.

The product of step (2) is, as mentioned above, a used probe which is typically a substantially double-stranded duplex whose constituent components are respectively (i) the first oligonucleotide and (ii) the second oligonucleotide with an additional nucleotide derived from the single nucleoside triphosphate and (iii) optionally the third oligonucleotide. Where step (2) is carried out in the presence of a ligase and the third oligonucleotide, (ii) and (iii) will together comprise a discrete fourth oligonucleotide and the used probe will be double-stranded in the vicinity of the recognition-site. If the second and third oligonucleotides have previously been joined together by a linker-region then it will be readily apparent that this will lead to a fourth oligonucleotide which is a closed-loop and highly resistant to exonucleolysis.

In step (3), the used probe is treated with a restriction endonuclease at a temperature in the range 20 to 100° C. In one embodiment, this restriction endonuclease is a nicking endonuclease designed to cut only the strand derived from the first oligonucleotide at the recognition-site. In another embodiment the restriction endonuclease may be one able to cut both strands and the second and/or third oligonucleotide may be rendered resistant to cleavage by the restriction endonuclease for example by inclusion of endonucleolytic blocking-groups in either or both of the second and third oligonucleotides. In one embodiment, these blocking-groups may be selected from phosphorothioate linkages and other backbone modifications commonly used in the art, oligonucleotide spacers, phosphate groups, or the like. In a third embodiment, where no ligase is employed, the restriction endonuclease is one able to cut both strands and which has a cutting site on the 3' side of the captured nucleotide (i.e. at the nick remaining between the second and third oligonucleotides after the capture of the nucleotide).

Details of suitable restriction endonucleases, including nicking endonucleases, which can be used with the method, probes and probes of the present invention can be found at the Rebase® database associated therewith.

Step (3) results in the strand derived from the first oligonucleotide being cleaved into two separate components one of which bears the fluorophores and, if employed, the quenchers. Thereafter, in step (4) this component, now susceptible to exonucleolysis, is digested by an enzyme exhibiting either 3'-5' or 5'-3' exonucleolytic activity according to which of the particular methods described above is being followed. Thus, as endonucleolysis and subsequent exonucleolysis occurs, the observer sees the onset of and a rapid growth in the fluorescence signal. The characteristics of this fluorescence then indirectly reflect the nature of the single nucleoside triphosphate originally captured by the relevant probe. Step (4) can most effectively be achieved at a temperature in the range 30 to 100° C.

In one embodiment it is preferred that step (3) is carried out at a higher temperature than step (2) and/or that step (4) is carried out at a higher temperature than step (3).

Thereafter, and in step (5), the fluorophores liberated in step (4), for example via the various iterations of step (2) and (3), are detected and the nature of the nucleobase attached to the single nucleoside triphosphate determined by inference. By carrying out the method of the invention systematically for all the single nucleoside triphosphates in the stream generated in step (1), data characteristic of the sequence of the original nucleic acid analyte can be generated and analysed. Methods of doing this are well-known in the art; for example the reaction medium can be interrogated with light from a laser or like source of high-intensity electromagnetic radiation and any fluorescence generated detected using a photodetector or an equivalent device tuned to the characteristic fluorescence wavelength(s) or wavelength envelope(s) of the various fluorophores. This in turn causes the photodetector to generate a characteristic electrical signal which can be processed and analysed in a computer using known algorithms.

As mentioned above, in one preferred embodiment, at the end of step (3) the second oligonucleotide with its associated captured nucleotide and optionally the third oligonucleotide or, if a ligase is employed, the fourth oligonucleotide derived from the used probe, is caused to hybridise to or otherwise complex with another corresponding first oligonucleotide molecule thereby producing a new oligonucleotide duplex corresponding to, i.e. having the same chemical and physical structure, as the original used probe. This product is then subject to a repeat of step (3) thereby releasing further fluorophores in a detectable state and again regenerating the fourth oligonucleotide or second oligonucleotide with captured nucleotide and optionally an associated third oligonucleotide. By this means, steps (2) and (3) are allowed to iterate causing further enhancement in the fluorescence signal; in principle until substantially all of the relevant first oligonucleotide has been consumed. In one embodiment, step (4) is carried out concurrently with each iteration of steps (2) and (3) while in another embodiment steps (2) and (3) are first iterated to produce a plurality of nicked first oligonucleotides which are then simultaneously subjected to exonucleolysis in step (4). As a consequence of any of these embodiments, the observer sees a much greater enhancement of the fluorescence signal than might otherwise have been obtained.

In one particularly preferred embodiment, the method of the present invention is carried out wholly or partially in a stream of microdroplets, at least some of which contain a single nucleoside triphosphate; suitably a stream whose ordering reflects the original nucleotide sequence of the analyte. Such a method may begin, for example, by inserting the nucleoside triphosphates generated in step (1) one-by-one into a corresponding stream of aqueous microdroplets maintained in an immiscible carrier solvent such as a hydrocarbon or silicone oil to help preserve the ordering. Alternatively, this can be achieved by directly creating the microdroplets downstream of the digestion (pyrophosphorolysis) zone; for example, by causing the reaction medium to emerge from a microdroplet head of suitable dimensions into a flowing stream of the solvent. Alternatively, small aliquots of the reaction medium from step (1) can be regularly and sequentially injected into a stream of pre-existing aqueous microdroplets suspended in the solvent. If this latter approach is adopted, each microdroplet may already contain the various components of the probe(s) together with the enzymes and any other reagents (e.g. buffer) required to effect steps (2) to (4). In yet another approach, the microdroplets created in the former embodiment can be caused to coalesce subsequently with a stream of such pre-existing microdroplets to achieve a similar outcome. In these microdroplet methods, step (5) then preferably involves delivering the microdroplets to a storage area and interrogating each microdroplet to identify the fluorophores liberated. Thereafter, the results obtained from each microdroplet are assembled into a stream of data characteristic of the sequence of the original nucleic acid analyte.

To avoid the risk that a given microdroplet contains more than one nucleoside triphosphate, it is preferred to release each nucleoside triphosphate in step (1) at a rate such that each filled microdroplet is separated on average by from 1 to 20 preferably 2 to 10 empty ones. Thereafter, the stream of filled and unfilled microdroplets in the solvent is caused to flow along a flow path, suitably a microfluidic flow path, at a rate and in a manner such that they are maintained in a discrete state and do not have the opportunity to coalesce with each other. Suitably, the microdroplets employed have a finite diameter less than 100 microns, preferably less than 50 microns, more preferably less than 20 microns and even more preferably less than 15 microns. Most preferably of all, their diameters are in the range 2 to 20 microns. In one embodiment, the microdroplet flow rate through the whole system is in the range 50 to 3000 microdroplets per second preferably 100 to 2000.

In a third aspect of the invention there is also provided a multi-component biological probe characterised by comprising (a) a first single-stranded oligonucleotide including an exonuclease blocking-site, a restriction endonuclease recognition-site located on the 5' side of the blocking-site and including a single nucleotide capture-site for capturing a single nucleoside triphosphate, and at least one fluorophore region located on the 5' side of the recognition-site and arranged so as to render the fluorophore(s) quenched and (b) a second and optionally a third single-stranded oligonucleotide capable of hybridising to complementary regions on the first oligonucleotide either side of the capture-site.

In one embodiment, the exonuclease blocking-site is located adjacent the 3' end of the first oligonucleotide. In another embodiment, the exonuclease blocking-site is achieved by making the first oligonucleotide circular; i.e. a closed-loop.

In a fourth aspect of the invention there is also provided a multi-component biological probe characterised by comprising (a) a first single-stranded oligonucleotide including an exonuclease blocking-site, a restriction endonuclease recognition-site located on the 3' side of the blocking-site and including a single nucleotide capture-site for capturing a single nucleoside triphosphate, and at least one fluorophore region located on the 3' side of the recognition-site and arranged so as to render the fluorophore(s) quenched and (b) a second and optionally a third single-stranded oligonucleotide capable of hybridising to complementary regions on the first oligonucleotide either side of the capture-site.

In one embodiment, the exonuclease blocking-site is located adjacent the 5' end of the first oligonucleotide. In another, the exonuclease blocking-site is achieved by making the first oligonucleotide circular; i.e. a closed-loop.

Preferably in both the second and third embodiments both a second and a third oligonucleotide are present.

In one embodiment of both of these third and fourth aspects, the fluorophores on the first oligonucleotide are arranged in close proximity to one another in order to self-quench. In another, the first oligonucleotide includes quencher(s) to quench the fluorophores in the fluorophore region. Suitable fluorophores and quenchers include but are not limited to those described above. In another embodiment, the second and third oligonucleotides are connected by a linker-region as explained above; with the linker-region itself preferably being another oligonucleotide region.

As explained above, for the purposes of DNA or RNA sequencing, the biological probes described herein can be assembled into a corresponding biological probe system comprised of a multiplicity of different first oligonucleotide types differing only in the nucleobase characteristic of the capture-site and the fluorophore used. In one embodiment, from one, two, three, four or more different first oligonucleotide types differing only in the nucleobase characteristic of a capture-site and the fluorophore(s) can be used. For naturally-occurring DNA or RNA, these nucleobases will be comprised of A, G, C, and T or U. In another embodiment, the biological probe system is made manifest as a kit further comprising at least one of a ligase, a polymerase, a restriction endonuclease and an enzyme exhibiting 3'-5' or 5'-3' exonucleolytic activity as the case may be.

The detection method used in the sequencing method described above is also generally applicable to the analysis, characterisation or quantification of single nucleoside triphosphates in a biological sample or a nucleic acid analyte derived therefrom by applying only steps (2) to (5) of the methods described above to a or each single nucleoside triphosphate constituent thereof. In such additional applications, the nature of these steps (2) to (5) and the biological probes employed will suitably be as described herein.

The invention is now illustrated with reference to the following Examples.

EXAMPLE 1

Preparation and Use of a Probe

A single-stranded first oligonucleotide 1 was prepared, having the following nucleotide sequence: 5'-GCTGTGCCGGGCTCGTGTCTCTGCGTTTCTTGF-FQGTGTGCATTGCATAGGTTCACGA TAX-3' (SEQ ID NO:1) wherein A, C, G, and T represent nucleotides bearing the relevant characteristic nucleobase of DNA; F represents a deoxythymidine nucleotide (T) labelled with Atto 700 dye using conventional amine-attachment chemistry; Q represents a deoxythymidine nucleotide labelled with a BHQ-2 quencher and X represents an inverted 3' dT nucleotide. It further comprises a capture region (A nucleotide) at the $42^{nd}$ base from its 5' end, selective for capturing deoxythymidine triphosphate nucleotides (dTTPs) in a mixture of deoxynucleoside triphosphates (dNTPs), and the recognition sequence for the nicking restriction endonuclease Nb.BsrDI, 'NNCATTGC'.

Another single-stranded oligonucleotide 2, comprising an oligonucleotide region having a sequence complementary to the 3' region flanking the capture-site of the first oligonucleotide, and a single-stranded oligonucleotide 3, comprising an oligonucleotide region having a sequence complementary to the 5' region flanking the capture-site of the first oligonucleotide with a single base mismatch, a 5' phosphate group, and a 3' inverted dT nucleotide, were also prepared. They had the following nucleotide sequences:

```
Oligonucleotide 2:
                                    (SEQ ID NO: 2)
5'-CGTGAACCTATGCAA-3'

Oligonucleotide 3:
                                    (SEQ ID NO: 3)
5'-PGCGAACGTAAAATGTCATGGX-3'
``` wherein P represents the 5' phosphate group and X the inverted 3' dT nucleotide.

A reaction mixture comprising the probe was then prepared. It had a composition corresponding to that derived from the following formulation:
- 20 uL 5× buffer pH 8.0
- 10 uL oligonucleotide 1, 100 nM
- 10 uL oligonucleotide 2, 10 nM
- 10 uL oligonucleotide 3, 1000 nM
- 10 uL spermine solution, 10 mM
- 10 U Nb.BsrDI nicking endonuclease (ex. New England Biolabs Inc.)
- 3.5 U *E. coli* ligase
- 2.9 U Bst Large Fragment polymerase
- 2.7 U Platinum Pfx polymerase
- 6.7 U Thermostable Inorganic Pyrophosphatase
- 10 uL mixture of dNTPs, 0.25 nM
- Water to 100 uL wherein the 5× buffer comprised the following mixture:
- 25 uL Trizma Acetate, 1M, pH 8.0
- 50 uL aqueous Magnesium Acetate, 1M
- 25 uL aqueous Potassium Acetate, 1M
- 50 uL Triton X-100 surfactant (10%)
- 500 µg BSA
- Water to 1 ml Capture of the dTTPs and ligation of oligonucleotide 2 to oligonucleotide 3 to form a used probe was then carried out by incubating the mixture at 37° C. for 10 minutes after which the temperature was increased to 56° C. for a further 120 minutes to allow iterated cleaving of the first oligonucleotide. The temperature was then increased to 72° C. for a further 15 minutes to allow digestion of the cleaved first oligonucleotide components bearing the fluorophores and quenchers. The fluorescence intensity of the Atto700 dye in the reaction mixture was measured using a CLARIOStar microplate reader (ex. BMG Labtech) as the reaction proceeded.

The growth in intensity of fluorescence over the final 15 minute digestion step was monitored in the presence and absence of the dNTP component of the reaction and the results shown graphically in FIG. 1. From this it can be seen that the probe efficiently captures the dTTPs and the cyclic nature of the process of the present invention leads to a rapid growth in fluorescence signal. On the contrary, in a comparative experiment where no dNTPs were present in the reaction mixture the Atto 700 dye on oligonucleotide 1 did not exhibit fluorescence to any significant extent.

EXAMPLE 2

Droplet Microfluidic Method Using the Probe

Figure 2:
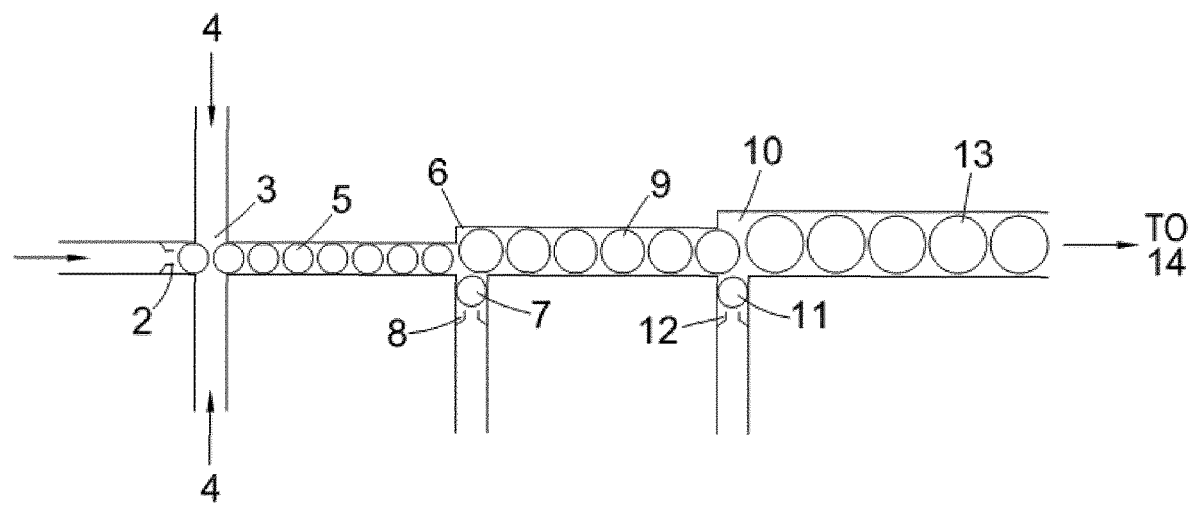

FIG. 2 schematically illustrates a microfluidic sequencing device in which microdroplets each containing a single nucleotide base are made to undergo reaction with a probe of the type above as described above.

An aqueous medium 1 comprising a stream of single nucleotide triphosphates obtained by the progressive pyrophosphorolysis of a 100 nucleotide base polynucleotide analyte derived from human DNA is caused to flow through a ten micron diameter microfluidic tube fabricated from PDMS polymer. The pyrophosphorolysis reaction itself is carried out by passing a stream of an aqueous, buffered (pH 7.5) reaction medium at 72° C., comprising Bst polymerase and a solution having a 2 millimoles per litre concentration of each of sodium pyrophosphate and magnesium chloride, over a glass micro bead onto which the analyte has been previously attached by means of a succinyl bridge. The order of the single nucleotides in 1, which is downstream of the micro bead, corresponds to the sequence of the analyte. 1 emerges from a droplet head 2 into a first chamber 3 where it is contacted with one or more streams of immiscible light silicone oil 4. The velocities of these streams are chosen to avoid turbulent mixing and to create aqueous spherical droplets 5 suspended in the oil each having a diameter of approximately eight microns. Typically, rates are adjusted so that between adjacent filled droplets there are on average 10 empty ones. A stream of 5 is then carried forward along a second microfluidic tube of the same diameter to a second chamber 6 into which a second stream of five micron aqueous spherical droplets 7 is also fed by means of a second droplet head 8. Droplets 5 and 7 are caused to coalesce in a sequential fashion to form enlarged aqueous droplets 9 approximately nine microns in diameter. Each of 7 contains inorganic pyrophosphatase to destroy any residual pyrophosphate anion present in each of 5.

A stream of 9 is then carried forward at the same rate via microfluidic tubing into a third chamber 10 where these droplets are contacted with a third stream of five micron aqueous spherical droplets 11 also fed thereto through a corresponding droplet head 12. The time taken for each of 9 to move between chambers 6 and 10 is c.2 minutes.

Droplets 9 and 11 are then caused to coalesce in 10 to produce droplets 13 (approximately ten microns in diameter). Each of 11 contains a mesophilic ligase, a thermophilic polymerase having 3'-5' exonuclease activity, the nicking restriction endonuclease Nb.BsrDI (ex. New England Biolabs Inc.) and a probe system comprising four sets of single-stranded oligonucleotides similar to those described in Example 1 each having a different first oligonucleotide labelled with a different fluorophore as explained above.

The stream of the coalesced microdroplets 13 so formed is then subjected to incubation at 37° C. for 10 minutes followed by 56° C. for 120 minutes and then 72° C. for 15 minutes. At the end of this time 13 is transferred to the detection system 14.

The detection system (not shown) typically comprises a detection window in which each droplet is interrogated with incident light from a laser. Action of this light then causes the released fluorophores in each droplet to fluoresce in a way characteristic of the single nucleotide base which was originally incorporated into the completed probe (or essentially not at all if the droplet was originally empty). The presence or absence of this fluorescence is then detected at the four characteristic wavelengths of the four fluorophores associated with the four oligonucleotide sets mentioned above. Thus as the droplets are interrogated in turn the sequence of nucleotide bases in the original polynucleotide analyte can in effect be read off.

---

The invention claimed is:

1. A method of sequencing a nucleic acid comprising the steps of:
   (1) generating a stream of single nucleoside triphosphates by progressive enzymatic digestion of the nucleic acid;
   (2) producing at least one used oligonucleotide probe by reacting, in the presence of a polymerase, at least one of the single nucleoside triphosphates with a corresponding biological probe comprising (a) a first single-stranded oligonucleotide including an exonuclease blocking-site, a restriction endonuclease recognition-site located on the 5' side of the blocking-site and including a single nucleotide capture-site for capturing the single nucleoside triphosphate, and at least one fluorophore region located on the 5' side of the recognition-site comprising fluorophore(s) arranged so as to render the fluorophore(s) quenched, wherein the fluorophore(s) are arranged in close proximity to one another in order to self-quench or wherein the at least one fluorophore region further comprises a quencher configured to quench the fluorophore(s), and (b) a second and a third single-stranded oligonucleotide each separate from the first oligonucleotide and capable of hybridising to complementary regions on the first oligonucleotide flanking the 3' and 5' sides of the capture-site;
   (3) cleaving the first oligonucleotide strand of the used probe at the recognition-site with a restriction endonuclease to create a first oligonucleotide component bearing the fluorophore(s);
   (4) digesting the first oligonucleotide component with an enzyme having 3'-5' exonucleolytic activity to yield fluorophore(s) in a detectable state; and
   (5) detecting the fluorophore(s) released in step (4);
   wherein the restriction endonuclease is a nicking endonuclease adapted to cleave only the first oligonucleotide; and
   wherein steps (2) and (3) are iterated and step (4) is carried out after the iteration.

2. The method of claim 1 wherein step (2) is carried out in the presence of a ligase to create a substantially double-stranded used probe in the vicinity of the recognition-site.

3. The method of claim 1 wherein the exonuclease blocking-site is achieved by making the first oligonucleotide a closed-loop or by including a double-stranded region therein.

4. The method of claim 1 wherein the second oligonucleotide and the third oligonucleotide are connected by a linker-region.

5. The method of claim 1 wherein the second and/or third oligonucleotide is resistant to cleavage by the restriction endonuclease.

6. The method of claim 1 wherein the at least one fluorophore region includes quenchers to quench the fluorophore(s).

7. The method of claim 1 wherein step (3) is carried out at a higher temperature than step (2) and/or that step (4) is carried out at a higher temperature than step (3).

8. The method of claim 1 wherein the probe comprises a system of up to four different first oligonucleotide types each having a different capture-site selective for a different one of the characteristic nucleobases of naturally-occurring or synthetic DNA or RNA and different characteristic fluorophore(s).

9. The method of claim 1 wherein step (1) further comprises containing each single nucleoside triphosphate in a corresponding microdroplet and that steps (2) to (5) are carried out in each microdroplet.

10. A method of sequencing a nucleic acid comprising the steps of:
    (1) generating a stream of single nucleoside triphosphates by progressive enzymatic digestion of the nucleic acid;
    (2) producing at least one used oligonucleotide probe by reacting, in the presence of a polymerase, at least one of the single nucleoside triphosphates with a corresponding biological probe comprising (a) a first single-stranded oligonucleotide including an exonuclease blocking-site, a restriction endonuclease recognition-site located on the 3' side of the blocking-site and including a single nucleotide capture-site for capturing the single nucleoside triphosphate, and at least one fluorophore region located on the 3' side of the recognition-site comprising fluorophore(s) arranged so as to render the fluorophore(s) quenched, wherein the fluorophore(s) are arranged in close proximity to one another in order to self-quench or wherein at least one fluorophore region further comprises a quencher configured to quench the fluorophore(s), and (b) a second and a third single-stranded oligonucleotide each separate from the first oligonucleotide and capable of hybridising to complementary regions on the first oligonucleotide flanking the 3' and 5' sides of the capture-site;
    (3) cleaving the first oligonucleotide strand of the used probe at the recognition-site with a restriction endonuclease to create a first oligonucleotide component bearing the fluorophore(s);
    (4) digesting the first oligonucleotide component with an enzyme having 5'-3' exonucleolytic activity to yield fluorophore(s) in a detectable state; and
    (5) detecting the fluorophore(s) released in step (4).

* * * * *

SEQUENCE LISTING

```
<160> NUMBER OF SEQ ID NOS: 3

<210> SEQ ID NO 1
<211> LENGTH: 61
<212> TYPE: DNA
<213> ORGANISM: Artificial sequence
<220> FEATURE:
<223> OTHER INFORMATION: single-stranded first oligonucleotide 1
<220> FEATURE:
<221> NAME/KEY: T labelled with Atto 700 dye
<222> LOCATION: (33)..(34)
<223> OTHER INFORMATION: F represents a deoxythymidine nucleotide (T)
      labelled with Atto 700 dye
<220> FEATURE:
<221> NAME/KEY: T labelled with a BHQ-2 quencher
<222> LOCATION: (35)..(35)
<223> OTHER INFORMATION: Q represents a deoxythymidine nucleotide
      labelled with a BHQ-2 quencher
<220> FEATURE:
<221> NAME/KEY: inverted 3' dT nucleotide
<222> LOCATION: (61)..(61)
<223> OTHER INFORMATION: X represents an inverted 3' dT nucleotide

<400> SEQUENCE: 1
gctgtgccgg gctcgtgtct ctgcgtttct tgtttgtgtg cattgcatag gttcacgata        60
t                                                                        61

<210> SEQ ID NO 2
<211> LENGTH: 15
<212> TYPE: DNA
<213> ORGANISM: Artificial sequence
<220> FEATURE:
<223> OTHER INFORMATION: single-stranded oligonucleotide 2

<400> SEQUENCE: 2
cgtgaaccta tgcaa                                                         15

<210> SEQ ID NO 3
<211> LENGTH: 21
<212> TYPE: DNA
<213> ORGANISM: Artificial sequence
<220> FEATURE:
<223> OTHER INFORMATION: single-stranded oligonucleotide 3
<220> FEATURE:
<221> NAME/KEY: 5' phosphate group
<222> LOCATION: (1)..(1)
<223> OTHER INFORMATION: 5' phosphate group
<220> FEATURE:
<221> NAME/KEY: 3' inverted dT nucleotide
<222> LOCATION: (21)..(21)
<223> OTHER INFORMATION: X represents 3' inverted dT nucleotide

<400> SEQUENCE: 3
gcgaacgtaa aatgtcatgg t                                                  21
```